(12) United States Patent
Park et al.

(10) Patent No.: US 11,320,392 B2
(45) Date of Patent: May 3, 2022

(54) HEAVY METAL DETECTING SENSOR, AND MANUFACTURING METHOD OF THE SAME, AND HEAVY METAL DETECTING METHOD

(71) Applicant: Korea University Research and Business Foundation, Sejong Campus, Sejong-si (KR)

(72) Inventors: Jin Sung Park, Guri-si (KR); Joo Hyung Park, Seoul (KR); Won Seok Lee, Seoul (KR); Gyu Do Lee, Namyangju-si (KR)

(73) Assignee: Korea University Research and Business Foundation, Sejong Campus, Sejong (KR)

( * ) Notice: Subject to any disclaimer, the term of this patent is extended or adjusted under 35 U.S.C. 154(b) by 129 days.

(21) Appl. No.: 16/657,332

(22) Filed: Oct. 18, 2019

(65) Prior Publication Data

US 2020/0124561 A1 Apr. 23, 2020

(30) Foreign Application Priority Data

Oct. 18, 2018 (KR) .......................... 10-2018-0124131

(51) Int. Cl.
*G01N 27/30* (2006.01)
*G01N 33/18* (2006.01)

(52) U.S. Cl.
CPC ....... *G01N 27/308* (2013.01); *G01N 33/1813* (2013.01)

(58) Field of Classification Search
CPC ............. G01N 27/327; G01N 27/3275; G01N 27/3277; G01N 33/1813; G01N 27/4035; G01N 27/308
See application file for complete search history.

(56) References Cited

U.S. PATENT DOCUMENTS

2014/0262832 A1  9/2014  Gunasekaran et al.

FOREIGN PATENT DOCUMENTS

KR         10-1659732 B1     9/2016
KR     10-2016-0132472 A    11/2016

OTHER PUBLICATIONS

Szymahska et al., "Electrochemical impedance spectroscopy for study of amyloid β-peptide interactions with (-) nicotine ditartrate and (-) cotinine," Biosensors and Bioelectronics 22 (2007) 1955-1960 (Year: 2007).*

Louise Serpell, "Review—Alzheimer's amyloid fibrils: structure and assembly," Biochimica et Biophysics Acts 1502 (2000) 16-30 (Year 2000).*

Suprun etsl., "Tyrosine Based Electrochemical Analysis of Amyloid-β Fragment (1016) Bridging to Metal(II) Ions," Electrochimica Acts 179 (2015) 93-99 (Year: 2015).*

(Continued)

*Primary Examiner* — Alexander S Noguerola
(74) *Attorney, Agent, or Firm* — Sughrue Mion, PLLC

(57) ABSTRACT

Provided is a heavy metal detecting sensor. The heavy metal detecting sensor includes an electrode and a plurality of amyloid fibers disposed on the electrode, wherein an amount of a redox current of the electrode decreases when the plurality of amyloid fibers react with heavy metal ions.

10 Claims, 19 Drawing Sheets
(14 of 19 Drawing Sheet(s) Filed in Color)

(56) References Cited

OTHER PUBLICATIONS

Bolisetty et al., "Gelation, Phase Behavior, and Dynamics of β-Lactoglobulin Amyloid Fibrils at Varying Concentrations and Ionic Strengths," Biomacromolecules 2012, 13, 3241-3251 (Year: 2012).*

Fuji et al.,"Electrochemical quantification of the Alzheimer's disease amyloid-β (1-40) using amyloid-β fibrillization promoting peptide," Sensing and Biosensing Research 6 (2015) 7-12 (Year: 2015).*

* cited by examiner

[Fig. 1]
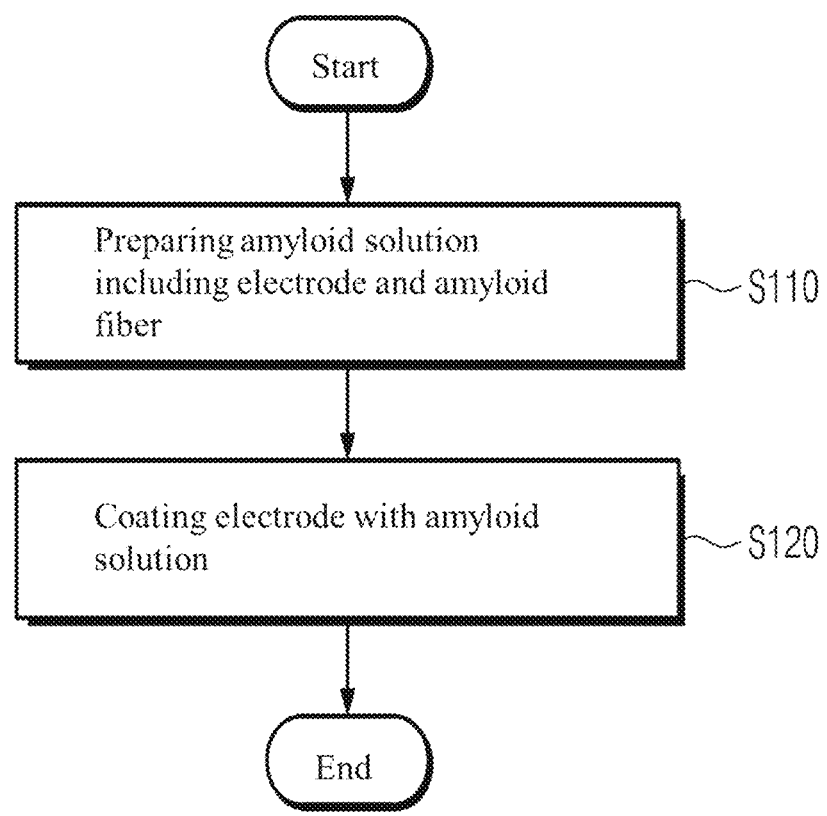

[Fig. 2]
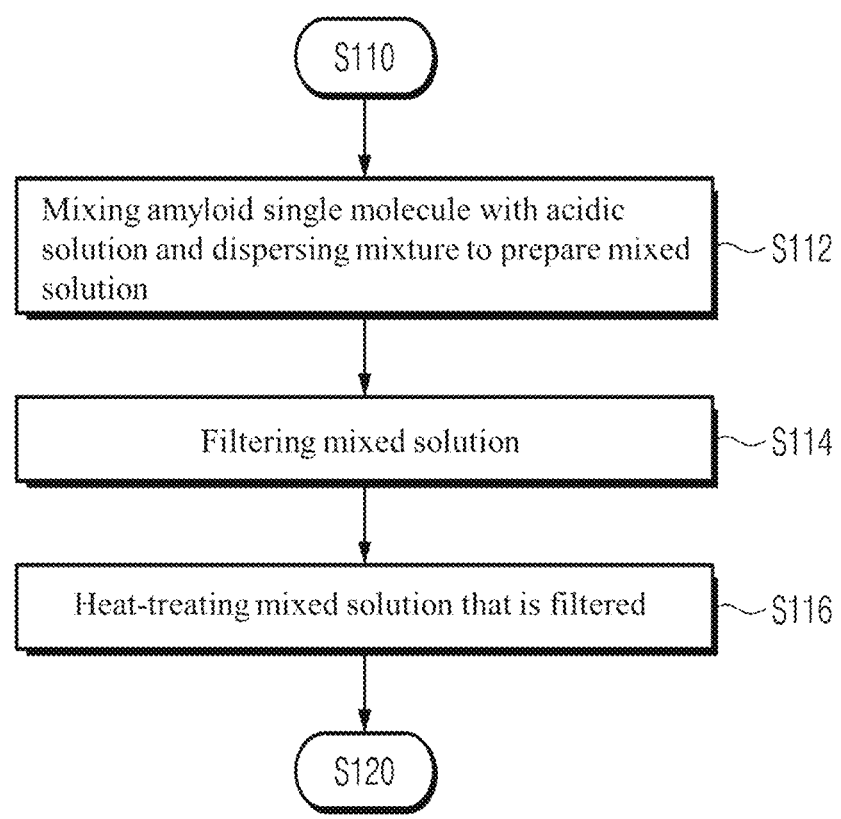

[Fig. 3]
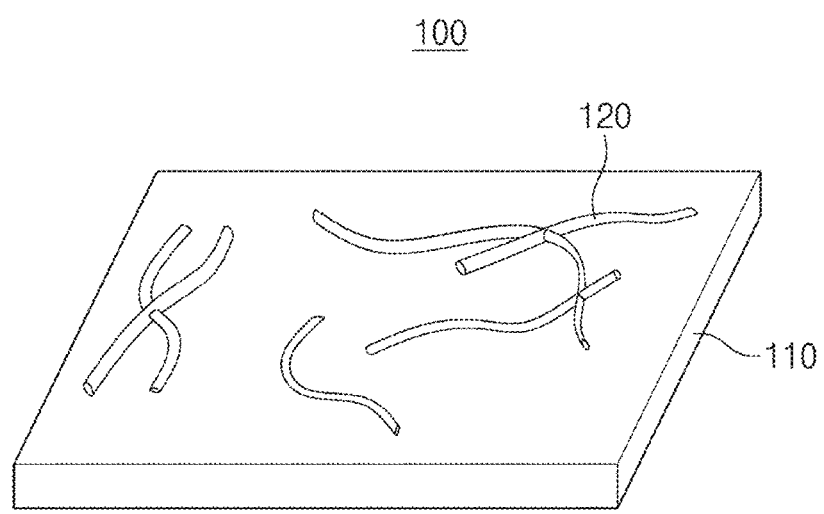

[Fig. 4A]
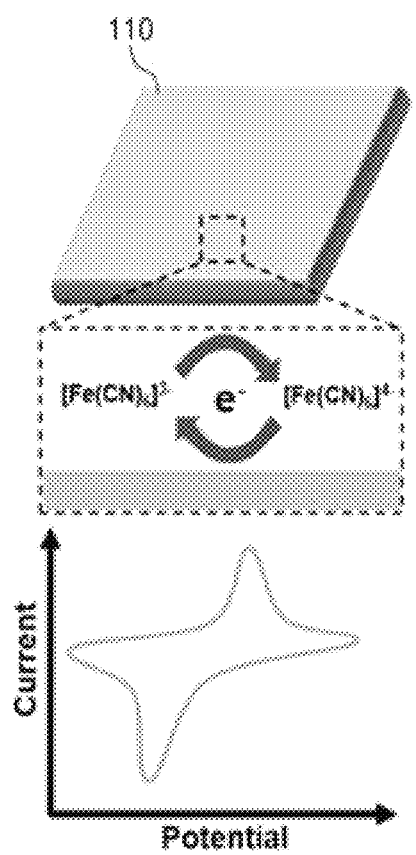

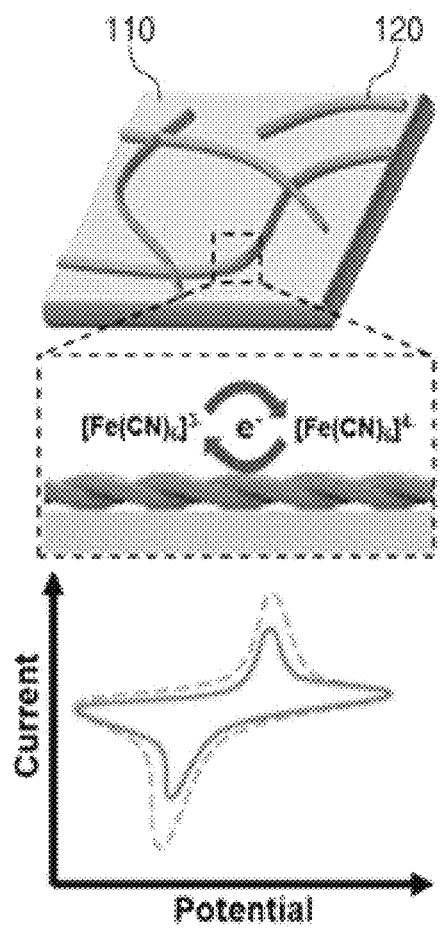
[Fig. 4B]

[Fig. 4C]
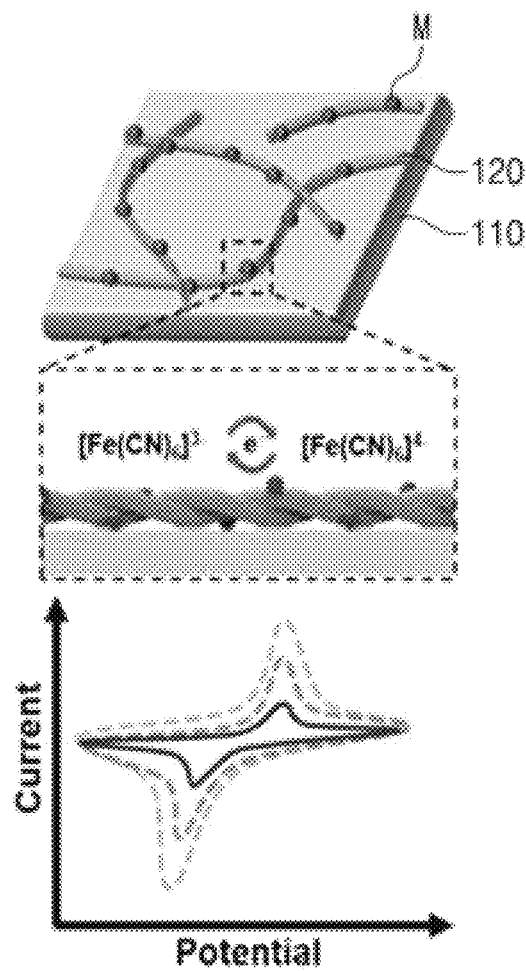

[Fig. 5A]
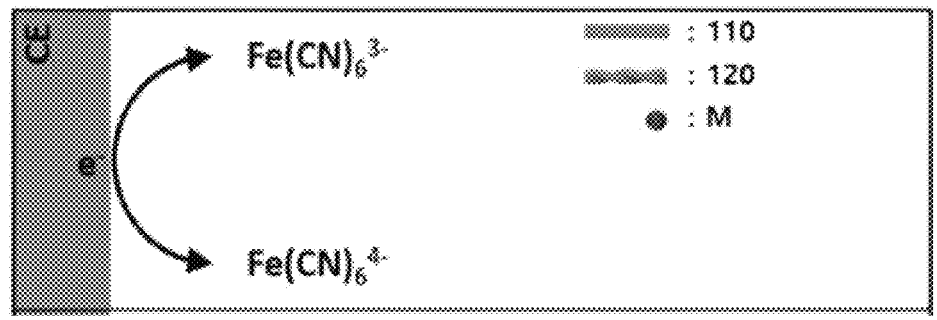
[Fig. 5B]
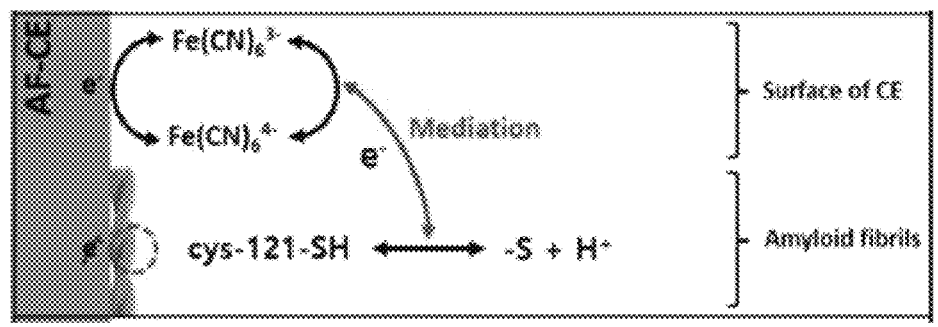
[Fig. 5C]
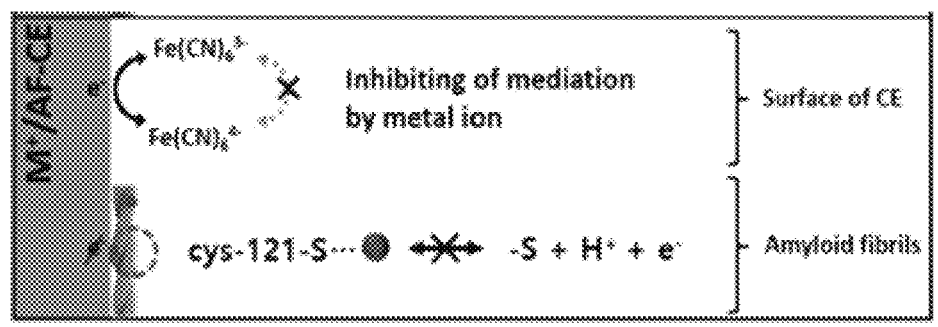

[Fig. 6A]
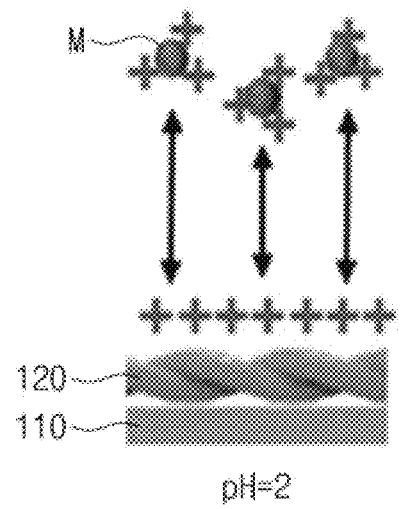
pH=2
[Fig. 6B]
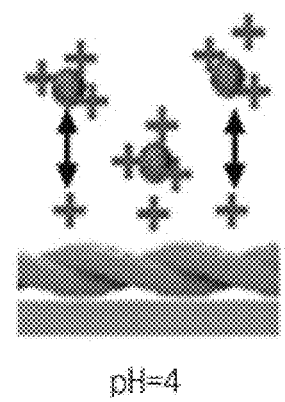
pH=4

[Fig. 6C]
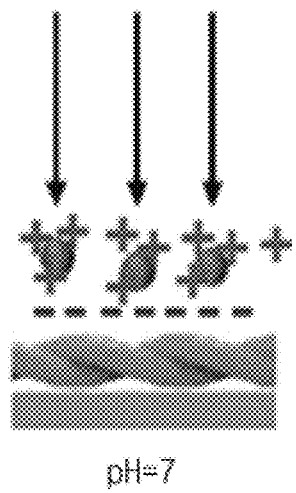
pH=7
[Fig. 6D]
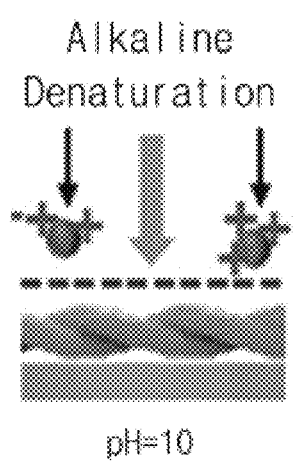
pH=10

[Fig. 7]
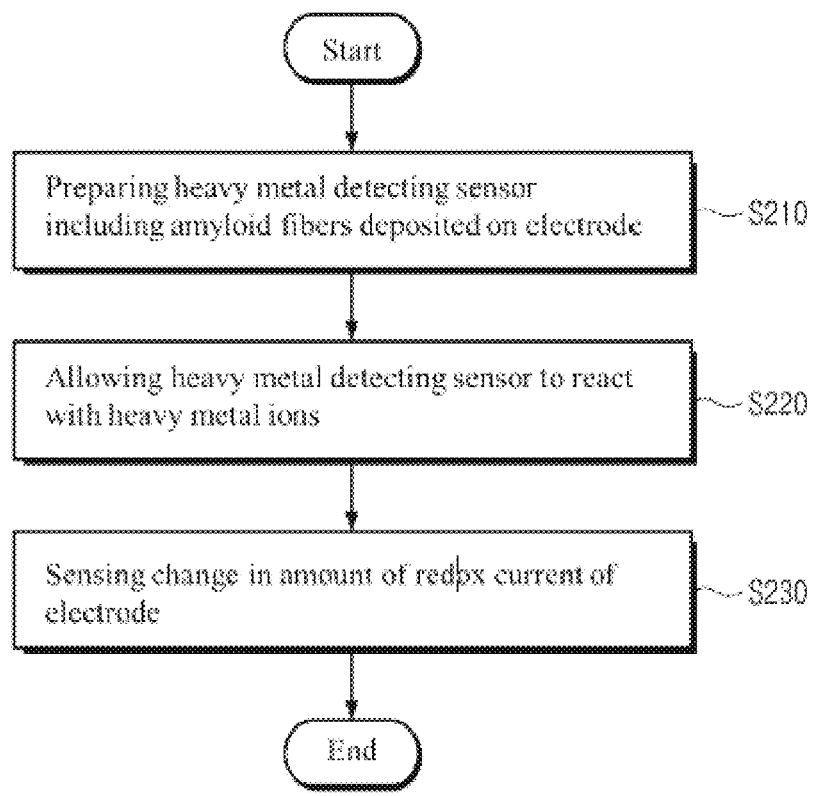

[Fig. 8A]
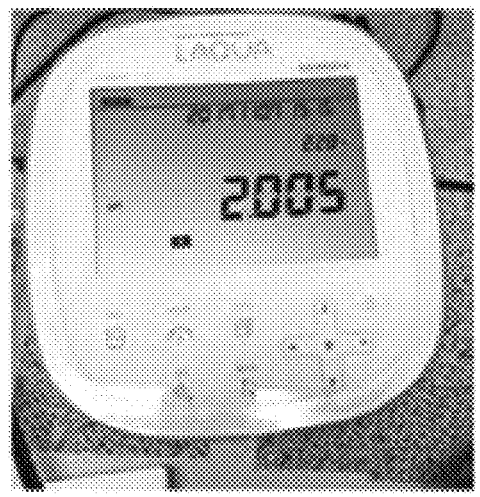
[Fig. 8B]

[Fig. 8C]
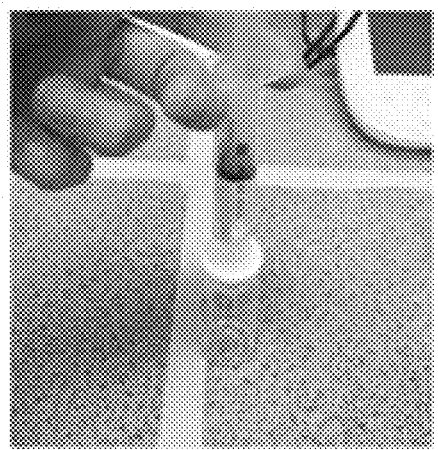
[Fig. 8D]

[Fig. 9]
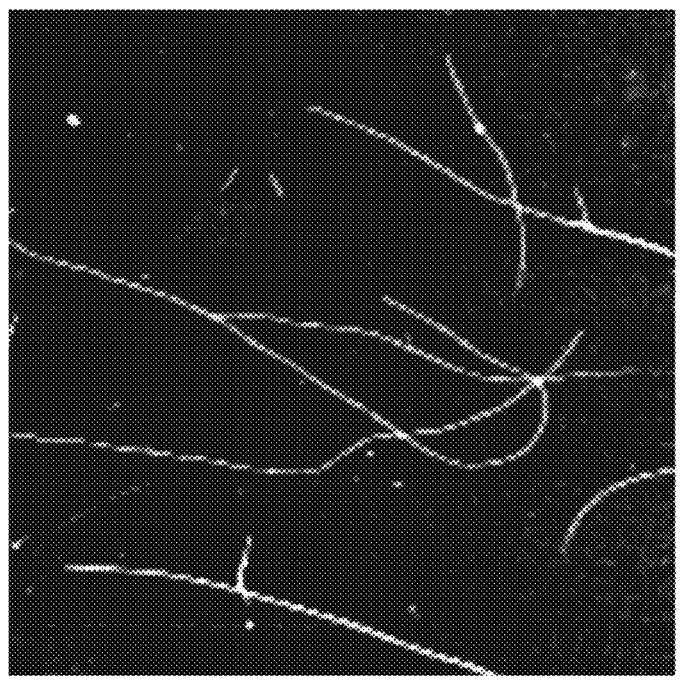

[Fig. 10]
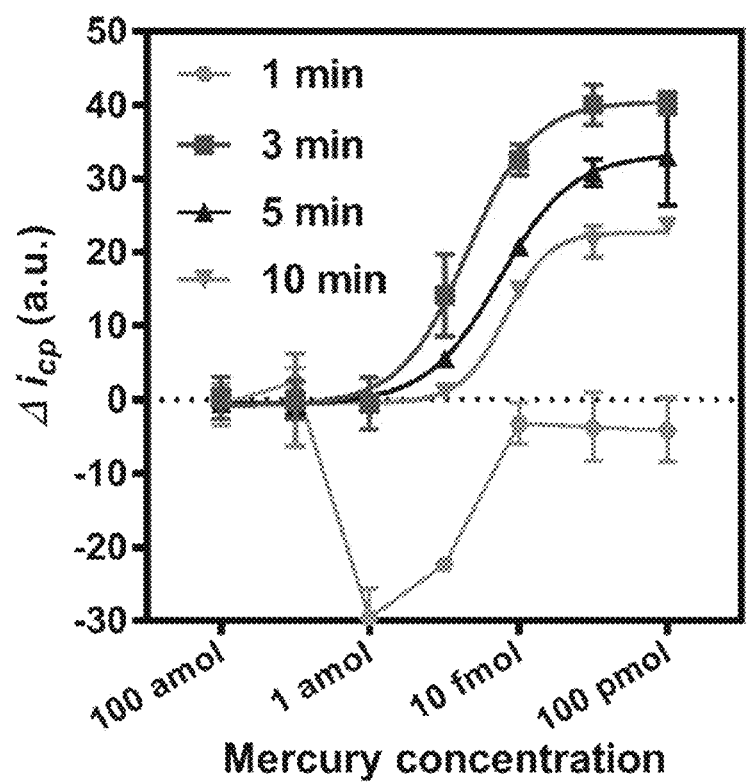

[Fig. 11]
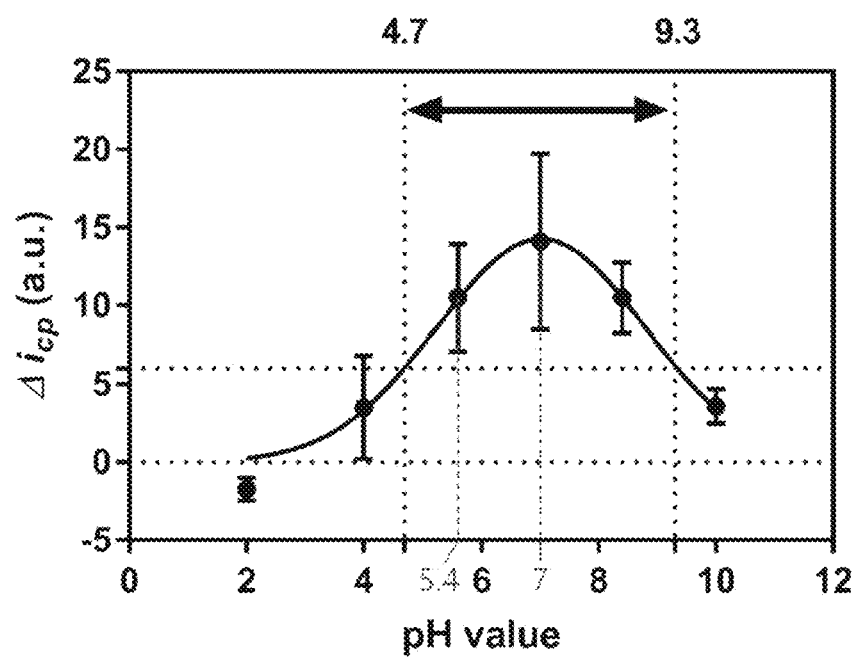

[Fig. 12]
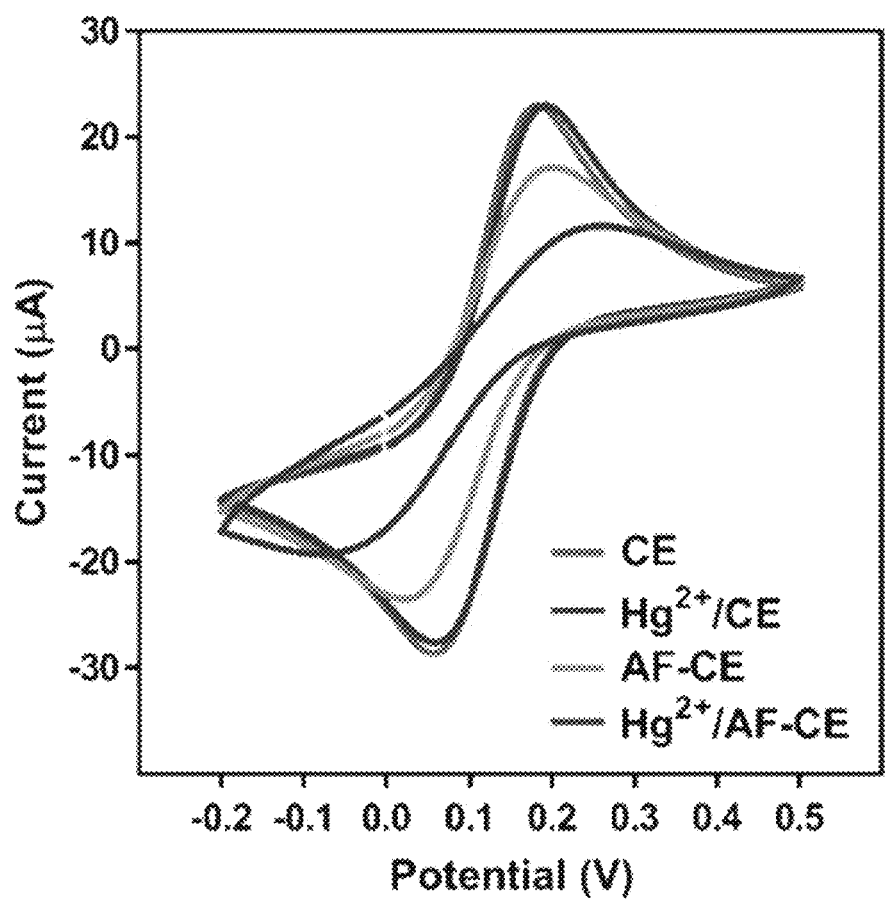

[Fig. 13]
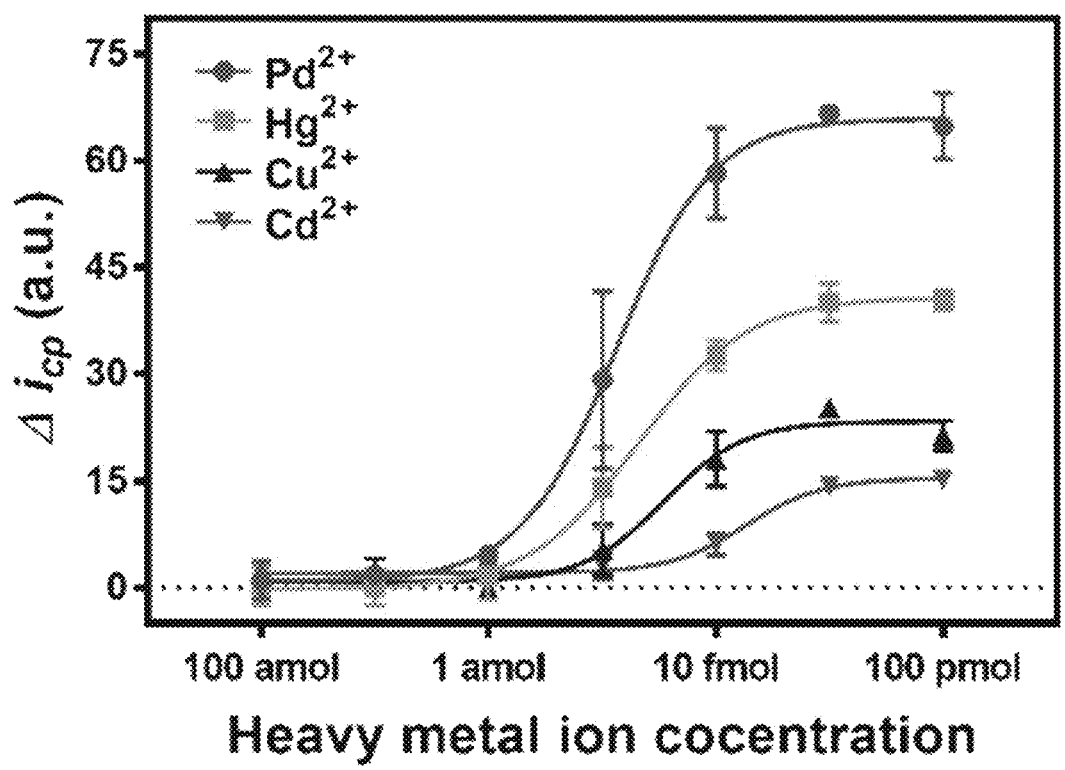

[Fig. 14A]
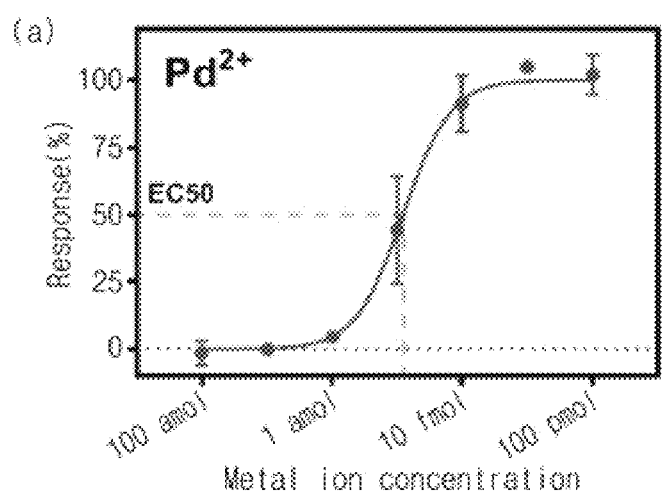
[Fig. 14B]
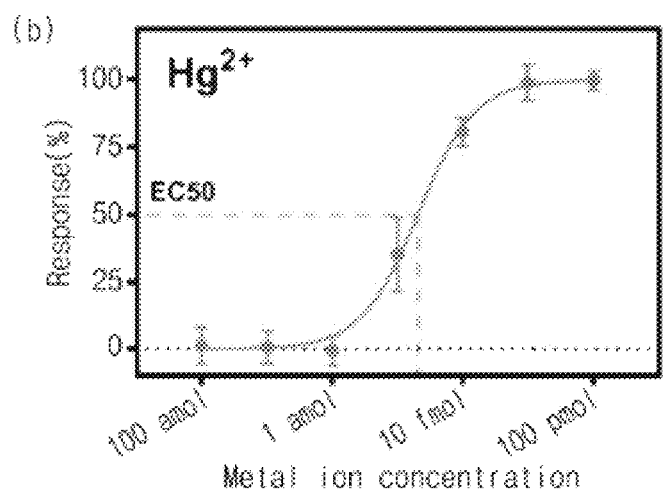

[Fig. 14C]
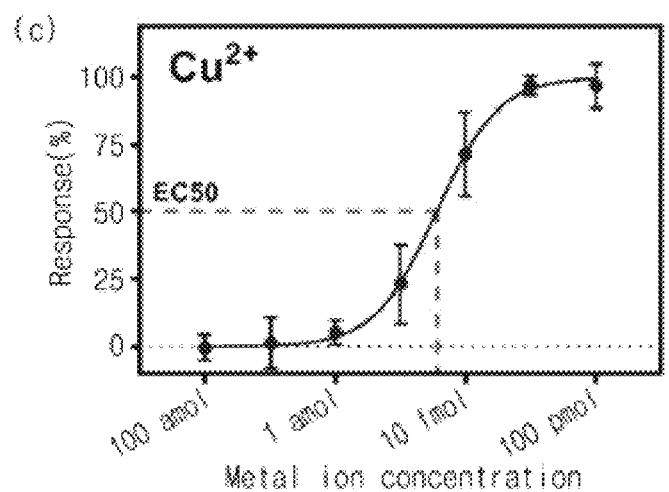
[Fig. 14D]
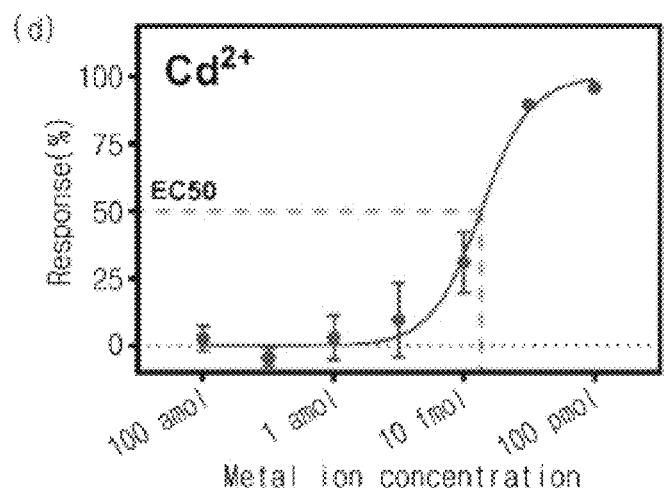

HEAVY METAL DETECTING SENSOR, AND MANUFACTURING METHOD OF THE SAME, AND HEAVY METAL DETECTING METHOD

BACKGROUND OF THE INVENTION

Field of the Invention

The present invention relates to a heavy metal detecting sensor, a method for manufacturing the same, and a heavy metal detecting method, and more particularly, to a heavy metal detecting sensor using a reaction between an amyloid fiber and a heavy metal, a manufacturing method thereof, and a heavy metal detecting method.

Description of the Prior Art

Recently, heavy metal ions, which are one of environmental pollutants, are known as inducers causing the biotoxicity and disease. In particular, the heavy metal ions dissolved in an aqueous solution may cause cytotoxicity, and it has been reported to cause neurodegenerative diseases such as Alzheimer's disease, Parkinson's disease and the like when the heavy metal ions are combined with amyloid fibers in the brain. Therefore, it is very important to detect target heavy metal ions to the extent of a low concentration with high selectivity.

A conventional representative technique for detecting trace heavy metals is an atomic absorption spectroscopy (AAS). However, the above technique is not only difficult to operate, but also uses measuring devices having a large volume, so it is required to prepare samples in the field and carry the samples to a laboratory for measurement. In particular, in the case of ASS, there are disadvantages in that it takes a long measurement time for detecting the heavy metals, a large amount of samples is required, and measurement samples have to be heat-treated at a high temperature. Accordingly, research and development are continuously performed regarding the technique that can overcome the above-mentioned disadvantages and detect the heavy metals within a short time using a small amount of samples.

SUMMARY OF THE INVENTION

A technical purpose of the present invention is to provide a heavy metal detecting sensor capable of detecting a heavy metal within a short time, a method for manufacturing the same, and a heavy metal detecting method.

Another technical purpose of the present invention is to provide a heavy metal detecting sensor capable of detecting a heavy metal even with a small amount of samples, a method of manufacturing the same, and a heavy metal detecting method.

Still another technical purpose of the present invention is to provide a heavy metal detecting sensor capable of detecting a heavy metal at a room temperature, a method of manufacturing the same, and a heavy metal detecting method.

The objectives of the present invention are not limited to the above-described ones.

In order to solve the above technical problem, the present invention provides a heavy metal detecting sensor.

According to one embodiment, the heavy metal detecting sensor may include an electrode and a plurality of amyloid fibers disposed on the electrode, wherein an amount of a redox current of the electrode decreases when the plurality of amyloid fibers react with heavy metal ions.

According to one embodiment, the amyloid fiber may include beta-lactoglobulin ($\beta$-lactoglobulin).

According to one embodiment, a redox reaction of cysteine contained in the amyloid fibers may be inhibited when the amyloid fibers react with the heavy metal ions.

According to one embodiment, the heavy metal ions may be provided in the form of a solution, and the solution including the heavy metal ions may have pH in the range of 5.4 to 7.

According to one embodiment, when the amyloid fibers react with the solution including the heavy metal ions, a surface of the amyloid fiber may have a negative charge.

According to one embodiment, the heavy metal ion may include at least one of a palladium ion ($Pd^{2+}$), a mercury ion ($Hg^{2+}$), a copper ion ($Cu^{2+}$), and a cadmium ion ($Cd^{2+}$).

According to one embodiment, the electrode may include carbon.

In order to solve the above technical problem, the present invention provides a heavy metal detecting method.

According to one embodiment, the heavy metal detecting method may include preparing a heavy metal detecting sensor including a plurality of amyloid fibers deposited on an electrode, allowing the heavy metal detecting sensor to react with heavy metal ions, and sensing a change in an amount of a redox current of the electrode, wherein the amount of the redox current of the electrode may decrease when the amyloid fibers of the heavy metal detecting sensor react with the heavy metal ions.

According to one embodiment, when the heavy metal detecting sensor reacts with the heavy metal ions, a redox reaction of cysteine contained in the amyloid fibers may be inhibited.

In order to solve the above technical problem, the present invention provides a method of manufacturing the heavy metal detecting sensor.

According to one embodiment, the method of manufacturing a heavy metal detecting sensor may include preparing an amyloid solution including an electrode and amyloid fibers, and coating the electrode with the amyloid solution.

According to one embodiment, the coating the electrode may be performed for a time of more than 1 minute and not more than 3 minutes.

According to one embodiment, the preparing the amyloid solution may include mixing an amyloid single molecule with an acidic solution and dispersing the mixture to prepare a mixed solution, filtering the mixed solution, and heat-treating the mixed solution that is filtered.

The heavy metal detecting sensor according to an embodiment of the present invention may include an electrode and a plurality of amyloid fibers disposed on the electrode, and the amount of a redox current of the electrode may decrease when the plurality of amyloid fibers react with heavy metal ions. Accordingly, the heavy metal detecting sensor capable of detecting a heavy metal by simply measuring the amount of the redox current of the electrode can be provided. In addition, as described above, the heavy metal detecting sensor according to an embodiment can detect the heavy metal by measuring the amount of the redox current of the electrode, so there are advantages that the time required for detecting the heavy metal can be shortened and the measurement can be performed even with a small amount of samples.

BRIEF DESCRIPTION OF THE DRAWINGS

The Application file contains at least one drawing executed in color. Copies of this application with the color drawings will be provided by the Office upon request and payment of the necessary fee.

The above and other objects, features, and advantages of the present invention will be more apparent from the following detailed description taken in conjunction with the accompanying drawings, in which:

FIG. 1 is a flowchart illustrating a method of manufacturing a heavy metal detecting sensor according to an embodiment of the present invention.

FIG. 2 is a flowchart illustrating an operation of preparing an amyloid solution in a method of manufacturing a heavy metal detecting sensor according to an embodiment of the present invention.

FIG. 3 is a view illustrating a heavy metal detecting sensor according to an embodiment of the present invention.

FIGS. 4A, 4B, 4C and 5A, 5B, 5C are views for explaining the mechanism of a heavy metal detecting sensor according to an embodiment of the present invention.

FIGS. 6A, 6B, 6C and 6D are views illustrating a binding mechanism according to pH of heavy metal ions that react with a heavy metal detecting sensor according to an embodiment of the present invention.

FIG. 7 is a flowchart illustrating a heavy metal detecting method according to an embodiment of the present invention.

FIGS. 8A, 8B, 8C, 8D are photographic views illustrating an operation of preparing an amyloid solution in a method of manufacturing a heavy metal detecting sensor according to an embodiment of the present invention.

FIG. 9 is an optical photographic view illustrating an amyloid solution in the process of manufacturing a heavy metal detecting sensor according to an embodiment of the present invention.

FIG. 10 is a graph illustrating a change in an amount of current as a function of a coating time of amyloid fibers in the process of manufacturing a heavy metal detecting sensor according to an embodiment of the present invention.

FIG. 11 is a graph illustrating a change in an amount of current as a function of pH of heavy metal ions that react with a heavy metal detecting sensor according to an embodiment of the present invention.

FIG. 12 is a graph illustrating an amount of current reduction of a heavy metal detecting sensor according to an embodiment of the present invention.

FIGS. 13 and 14A, 14B, 14C, 14D are graphs illustrating a change in response of a heavy metal detecting sensor as a function of a type of heavy metal ions according to an embodiment of the present invention.

DETAILED DESCRIPTION OF THE EXEMPLARY EMBODIMENTS

Hereinafter, preferred embodiments of the present invention will be described in detail with reference to the accompanying drawings. However, the technical spirit of the present invention is not limited to the embodiments, but may be realized in different forms. The embodiments introduced here are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the thicknesses of the membrane and areas are exaggerated for efficient description of the technical contents.

Further, in the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combination thereof described in the specification are present, and may be understood that one or more other features, numbers, step, elements, or combinations thereof may be added.

Further, in the specification, the expression 'a constant length' or 'the same length' may be understood as meaning 'a substantially constant length' or 'substantially the same length'.

Further, in the following description of the present invention, a detailed description of known functions and configurations incorporated herein will be omitted when it may make the subject matter of the present invention unnecessarily unclear.

FIG. 1 is a flowchart illustrating a method of manufacturing a heavy metal detecting sensor according to an embodiment of the present invention, FIG. 2 is a flowchart illustrating an operation of preparing an amyloid solution in a method of manufacturing the heavy metal detecting sensor according to an embodiment of the present invention, and FIG. 3 is a view illustrating the heavy metal detecting sensor according to an embodiment of the present invention.

Referring to FIGS. 1 to 3, an electrode 110 and an amyloid solution are prepared (S110). According to one embodiment, the electrode 110 may include carbon. That is, the electrode 110 may be a carbon electrode. According to one embodiment, the amyloid fiber may include beta-lactoglobulin (β-lactoglobulin). Accordingly, there is an environmentally friendly advantage compared to a heavy metal detecting sensor including amyloid beta fibers.

According to one embodiment, the preparing of the amyloid solution may include mixing an amyloid single molecule with an acidic solution and dispersing the mixture to prepare a mixed solution (S112), filtering the mixed solution (S114), and heat-treating the mixed solution that is filtered (S116). Specifically, the preparing of the mixed solution (S112) may include mixing the amyloid single molecule with a pH 2 solution to have a concentration of 1 wt %, and then vortexing the mixture for 30 minutes. The filtering of the mixed solution (S114) may be performed by using a membrane filter having a size of 0.2 μm. The heat-treating of the mixed solution (S116) may be performed for 24 hours at a temperature of 90° C. Accordingly, the amyloid single molecule may be grown in the form of an amyloid fiber. As a result, the amyloid solution may include amyloid fibers.

The electrode 110 may be coated with the amyloid solution (S120). Accordingly, the heavy metal detecting sensor 100 according to an embodiment may be manufactured. When the electrode 110 is coated with the amyloid solution, an amyloid fiber 120 included in the amyloid solution may be deposited on the electrode 110. As a result, the heavy metal detecting sensor 100 according to the embodiment may have a configuration in which a plurality of amyloid fibers 120 are disposed on the electrode 110.

According to one embodiment, the coating of the amyloid solution may be performed for a time of more than 1 minute and not more than 3 minutes. On the contrary, when the coating of the amyloid solution is performed for a time of 1 minute or less, the amyloid fiber 120 included in the amyloid solution may not be easily deposited on the electrode 110. In this case, when the heavy metal detecting sensor, which will be described below, reacts with the heavy metal, a change in the amount of redox current of the electrode 110 may not be easily generated, thereby causing a problem in which the heavy metal may not be detected. Meanwhile, when the coating of the amyloid solution is performed for more than 3 minutes, the amyloid fiber 120 included in the amyloid solution may be deposited on the electrode 110 too thick. When the thickness of the amyloid fiber 120 deposited on the electrode 110 is too thick, the diffusion of electrons generated by the redox reaction may be limited. In this case, when the heavy metal detecting sensor, which will be described below, reacts with the heavy metal, a change in the amount of redox current of the electrode 110 may not be easily generated, thereby causing a problem in which the heavy metal may not be detected.

The heavy metal detecting sensor 100 according to the embodiment may detect the heavy metal ions by sensing a change in the amount of redox current of the electrode 110 when the plurality of amyloid fibers 120 react with the heavy metal ions. Hereinafter, a specific mechanism of the heavy metal detecting sensor 100 for detecting the heavy metal ions will be described with reference to FIGS. 4A, 4B, 4C and 5A, 5B, 5C.

FIGS. 4A, 4B, 4C and 5A, 5B, 5C are views for explaining the mechanism of the heavy metal detecting sensor according to an embodiment of the present invention.

Referring to FIG. 4A and FIG. 5A, electrons generated by the redox reaction of an electrolyte may freely diffuse in the electrode 110 in which the amyloid fiber 120 is not deposited. Accordingly, as shown in FIG. 4A, the CV curve representing the current according to the potential of the electrode may have a large area.

Meanwhile, referring to FIG. 4B and FIG. 5B, in the case of the heavy metal detecting sensor according to the embodiment in which the amyloid fiber 120 is deposited on the electrode 110, the diffusion of electrons may be interrupted by the amyloid fiber 120 which is a nonconductor. In addition, on the contrary, the electrons generated through the redox reaction of the cysteine included in the amyloid fiber may mediate the redox of the electrolyte, thereby promoting the redox reaction of the electrolyte to promote the diffusion of the electrons. That is, in the case of the heavy metal detecting sensor according to the embodiment, the amount of redox current of the electrode 110 may be reduced because the amyloid fiber 120 interrupts the electron diffusion, but the cysteine contained in the amyloid fiber 120 may promote the electron diffusion through the redox reaction, so that the amount of the redox current of the electrode 110 may increase. However, in the heavy metal detecting sensor according to the embodiment, the decrease in the amount of redox current due to the disturbance of the electron diffusion by the amyloid fiber 120 may be greater than the increase in the amount of redox current caused by the redox reaction of cysteine. Accordingly, the heavy metal detecting sensor according to the embodiment may reduce the amount of redox current compared to the electrode 110 where the amyloid fiber 120 is not deposited. This can be found through the reduction of the CV curve area in FIG. 4B.

Referring to FIG. 4C and (FIG. 5C, when the heavy metal detecting sensor according to the embodiment reacts with the heavy metal ions M, the heavy metal ions M may be combined with the amyloid fibers 120. Specifically, the heavy metal ions M may be combined with cysteine included in the amyloid fiber 120. In this case, the heavy metal ions M may inhibit the redox reaction of cysteine. Accordingly, a phenomenon, in which electrons generated through the redox reaction of the cysteine mediate the redox of the electrolyte to promote the diffusion of electrons, may be inhibited. As a result, when the heavy metal detecting sensor according to the embodiment reacts with the heavy metal ions M, the amount of redox current of the electrode 110 may be reduced than before the heavy metal detecting sensor reacts with the heavy metal ions M. That is, the heavy metal ions M may inhibit the increase in the amount of redox current caused by the redox reaction of cysteine, thereby reducing the total amount of redox current generated from the electrode 110. This can be found through the reduction of the CV curve area in FIG. 4C.

According to one embodiment, the heavy metal ions M may include at least one of palladium ions ($Pd^{2+}$), mercury ions ($Hg^{2+}$), copper ions ($Cu^{2+}$), and cadmium ions ($Cd^{2+}$). The kind of the heavy metal ions M may not be limited. In the heavy metal detecting sensor 100 according to the embodiment, the change in the amount of the redox current generated from the electrode 110 may vary depending on the type of the heavy metal ions M. For example, the amount of decrease in the redox current generated from the electrode 110 when the heavy metal detecting sensor 100 according to the embodiment reacts with the palladium ions ($Pd^{2+}$) may be different from the amount of decrease in the redox current generated from the electrode 110 when the heavy metal detecting sensor 100 reacts with the mercury ions ($Hg^{2+}$). Accordingly, the heavy metal detecting sensor 100 according to an embodiment of the present invention can detect the presence or absence of the heavy metal ions M by simply measuring the change in the amount of redox current generated from the electrode 110 and can detect the type of the heavy metal ions M by distinguishing the amount of change in the redox current generated from the electrode 110.

According to one embodiment, the heavy metal ions (M) may be provided in the form of a solution. In this case, pH of the solution including the heavy metal ions M may be in the range of 5.4 to 7. Thus, the heavy metal detecting sensor 100 according to the embodiment may easily detect the heavy metal ions M. That is, when the heavy metal detecting sensor 100 according to the embodiment reacts with the heavy metal ions M having pH in the range of 5.4 to 7, the heavy metal ions M and the amyloid fiber 120 may be easily combined with each other. Hereinafter, a mechanism for combining the amyloid fiber 120 according to the pH of the solution including the heavy metal ions M will be described with reference to FIGS. 6A-6D.

FIGS. 6A, 6B, 6C and 6D are views illustrating a binding mechanism according to the pH of the heavy metal ions that react with the heavy metal detecting sensor according to an embodiment of the present invention.

Referring to FIGS. 6A and 6B, when the pH of the solution including the heavy metal ions M is 2 and 4, both surfaces of the amyloid fiber 120 and the heavy metal ions M may have a positive charge so that they are not combined with each other. However, referring to FIG. 6C, when the pH of the solution including the heavy metal ions M is 7, the surface of the amyloid fiber 120 has a negative charge, so the amyloid fiber 120 may be easily combined with the heavy metal ions having the positive charge. Meanwhile, referring to FIG. 6D, when the pH of the solution including the heavy metal ions M is 10, the surface of the amyloid fiber 120 has the negative charge, but alkaline denaturation occurs so that the heavy metal ions M may not be easily combined.

That is, the pH of the heavy metal ions that react with the heavy metal detecting sensor according to the embodiment is preferably in the range of 5.4 to 7. When the pH is less than 5.4 or more than 7, the heavy metal ions M may not be easily combined with the amyloid fiber 120, so the detection of the heavy metal ion (M) may not be easily achieved.

The heavy metal detecting sensor 100 according to an embodiment of the present invention may include the electrode 110, and the plurality of amyloid fibers 120 disposed on the electrode 110, in which the amount of redox current of the electrode 110 may be reduced when the plurality of amyloid fibers 120 react with the heavy metal ions M. Accordingly, the heavy metal detecting sensor capable of detecting the heavy metal by simply measuring the amount of redox current of the electrode 110 may be provided. In addition, as described above, the heavy metal detecting sensor 100 according to the embodiment can detect the heavy metal by measuring the amount of redox current of the electrode 110, so there are advantages that the time required for detecting the heavy metal can be shortened and the measurement can be performed even with a small amount of samples.

The heavy metal detecting sensor and the manufacturing method thereof according to the embodiment of the present invention have been described above. Hereinafter, a heavy metal detecting method according to an embodiment of the present invention will be described.

FIG. 7 is a flowchart illustrating a heavy metal detecting method according to an embodiment of the present invention.

Referring to FIG. 7, the heavy metal detecting method may include preparing a heavy metal detecting sensor in which a plurality of amyloid fibers are deposited on an electrode (S210), allowing the heavy metal detecting sensor to react with heavy metal ions (S220), and sensing a change in an amount of a redox current of the electrode (S230). Hereinafter, each operation will be described in detail.

In operation S210, the heavy metal detecting sensor may be prepared. According to one embodiment, the heavy metal detecting sensor may be the same as the heavy metal detecting sensor according to the embodiment described with reference to FIG. 3. Thus, the heavy metal detecting sensor may have a configuration in which the plurality of amyloid fibers 120 are deposited on the electrode 110.

In operation S220, the heavy metal detecting sensor 100 may react with the heavy metal ions M. When the heavy metal detecting sensor 100 reacts with the heavy metal ions M, the heavy metal ions M may be combined with the amyloid fiber 120. As a result, the redox reaction of the cysteine included in the amyloid fiber 120 may be inhibited, thereby reducing the amount of redox current of the electrode 110. The mechanism of reducing the amount of redox current of the electrode 110 may be the same as the mechanism of reducing the amount of redox current of the heavy metal detecting sensor according to the embodiment described with reference to FIGS. 4A-4C and FIGS. 5A-5C. Accordingly, detailed description thereof will be omitted.

In operation S230, the amount of redox current of the electrode 110, which is changed as the heavy metal detecting sensor 100 reacts with the heavy metal ions M in operation S220, may be sensed. In detail, when the heavy metal ions M are combined with the amyloid fiber 120, the amount of redox current of the electrode 110 may be reduced. Therefore, the heavy metal detecting method according to the embodiment can detect the heavy metal by sensing the reduction in the amount of the redox current of the electrode 110.

The heavy metal detecting method according to the embodiment of the present invention has been described above. Hereinafter, specific experimental examples and characteristic evaluation results of the heavy metal detecting sensor and the method according to the embodiment of the present invention will be described.

FIGS. 8A, 8B, 8C, 8D are photographic views illustrating an operation of preparing an amyloid solution in a method of manufacturing a heavy metal detecting sensor according to an embodiment of the present invention and FIG. 9 is an optical photographic view illustrating an amyloid solution in the process of manufacturing a heavy metal detecting sensor according to an embodiment of the present invention.

Referring to FIGS. 8A-8D and 9, amyloid single molecules were mixed with a pH 2 solution to have a concentration of 1 wt %, and then the mixture was vortexed for 30 minutes. Then, the mixture was filtered using a membrane filter having a size of 0.2 μm and heat-treated at a temperature of 90° C. for 24 hours to prepare an amyloid solution. FIGS. 8A-8D are pictures taken in general for illustrating the pH, the vortexing process, the filtering process, and the heat treatment process of the solution mixed with the amyloid single molecule, and FIG. 9 is a picture of the prepared amyloid solution captured by an atomic force microscope (AFM). As can be seen in FIGS. 8A-8D and 9, the amyloid solution prepared by the method described above may include a plurality of amyloid fibers.

FIG. 10 is a graph illustrating a change in an amount of current as a function of a coating time of amyloid fibers in the process of manufacturing a heavy metal detecting sensor according to an embodiment of the present invention.

Referring to FIG. 10, after preparing four heavy metal detecting sensors coated with the amyloid fibers for different times of 1 minute, 3 minutes, 5 minutes, and 10 minutes, each heavy metal detecting sensor was reacted with mercury ions, and the decrease in the amount of current of the heavy metal detecting sensor was measured.

As can be seen from FIG. 10, in the case of a heavy metal detecting sensor coated with the amyloid fiber for a time of 1 minute, it was confirmed that no particular feature appears. This is considered as a phenomenon occurring when the electrode is not sufficiently coated with the amyloid fiber. In contrast, in the case of heavy metal detecting sensors coated with amyloid fibers for a time of 3 minutes, 5 minutes, and 10 minutes, all the heavy metal detecting sensors were reacted with mercury having concentrations of 100 amol, 1 amol, 10 fmol, and 100 pmol, and it was confirmed that the current was decreased. In particular, the heavy metal detecting sensor coated with the amyloid fiber for a time of 3 minutes represented the most sensitive reaction with mercury ions, and it was confirmed that the amount of current reduction was greatest in the heavy metal detecting sensor. Accordingly, when manufacturing the heavy metal detecting sensor according to the embodiment, it can be understood that the efficiency of the sensor may be improved by controlling the coating time of the amyloid to the level of more than 1 minute and not more than 3 minutes.

FIG. 11 is a graph illustrating a change in an amount of current as a function of pH of heavy metal ions that react with a heavy metal detecting sensor according to an embodiment of the present invention.

Referring to FIG. 11, the amount of current reduction in the heavy metal detecting sensor was measured after allowing the heavy metal detecting sensor to react with a mercury ion solution having different pH of 0 to 12.

As can be seen from FIG. 11, the amount of current reduction in the heavy metal detecting sensor according to the embodiment was increased gradually as the pH of the mercury ion solution increases and the amount of current reduction in the heavy metal detecting sensor was decreased from the time point of more than pH 7. In particular, it was confirmed that the amount of current reduction in the heavy metal detecting sensor was highest when the pH is in the range of 5.4 to 7. Accordingly, it can be understood that the heavy metal detecting sensor according to the embodiment exhibits the highest efficiency when the heavy metal detecting sensor reacts with a heavy metal ion solution having the pH in the range of 5.4 to 7.

FIG. 12 is a graph illustrating an amount of current reduction of a heavy metal detecting sensor according to an embodiment of the present invention.

Referring to FIG. 12, CV curves are illustrated by measuring current (μA) according to potential (V) in case of the electrode CE, in case when the electrode was reacted with mercury ions ($Hg^{2+}$/CE), in case of the heavy metal detecting sensor, in which the amyloid fiber is deposited on the electrode (AF-CE), and in case when the heavy metal detecting sensor, in which the amyloid fiber was deposited on the electrode, was reacted with mercury ions ($Hg^{2+}$/AF-CE). The difference in an area of the CV curve represents the amount of change in current, and the amount of current reduction increases as the area of the CV curve decreases.

As can be seen from FIG. 12, in case of the heavy metal detecting sensor (AF-CE), in which the amyloid fiber is deposited on the electrode, the area of the CV curve is reduced as compared with the case of the electrode CE. In addition, in case when the heavy metal detecting sensor was reacted with mercury ions ($Hg^{2+}$/AF-CE), the area of the CV curve is reduced as compared with the case of the heavy metal detecting sensor (AF-CE). That is, it can be understood that the amount of current is reduced when the heavy metal detecting sensor according to the embodiment reacts with the heavy metal ions, and the heavy metal ions can be detected by a method of measuring the amount of current reduction.

FIGS. 13 and 14A, 14B, 14C, 14D are graphs illustrating a change in response of a heavy metal detecting sensor as a function of a type of heavy metal ions according to an embodiment of the present invention.

Referring to FIG. 13, an amount of current reduction in the heavy metal detecting sensor according to the embodiment was measured after allowing the heavy metal detecting sensor to react with palladium ions ($Pd^{2+}$), mercury ions ($Hg^{2+}$), copper ions ($Cu^{2+}$), and cadmium ions ($Cd^{2+}$). As can be seen from FIG. 13, the heavy metal detecting sensor according to the embodiment represented the largest current reduction when reacting with the palladium ions ($Pd^{2+}$), followed by the mercury ions ($Hg^{2+}$), the copper ions ($Cu^{2+}$), and the cadmium ions ($Cd^{2+}$).

Referring to FIGS. 14A-14D, the heavy metal detecting sensor according to the embodiment was reacted with palladium ions ($Pd^{2+}$), mercury ions ($Hg^{2+}$, copper ions ($Cu^{2+}$), and cadmium ions ($Cd^{2+}$) and the response (%) is represented in a sigmoid graph. In FIG. 14, EC50 is a value representing the concentration corresponding to 50% of the response, and the response is sensitive as the value of the EC50 is lowered.

As can be seen from FIG. 14A, when the heavy metal detecting sensor according to the embodiment was reacted with palladium ions ($Pd^{2+}$), the EC50 value was 122.7 fmol.

In addition, when the heavy metal detecting sensor according to the embodiment was reacted with mercury ions ($Hg^{2+}$), the EC50 value was 198.7 fmol. Further, when the heavy metal detecting sensor according to the embodiment was reacted with copper ions ($Cu^{2+}$), the EC50 value was 345.2 fmol. When the heavy metal detecting sensor according to the embodiment was reacted with cadmium ions ($Cd^{2+}$), the EC50 value was 1858.0 fmol. That is, it can be understood that the heavy metal detecting sensor according to the embodiment represents the highest response with the palladium ions ($Pd^{2+}$).

Although the preferred embodiments of the present invention have been described in detail until now, the scope of the present invention is not limited to the embodiments and should be construed by the attached claims. Further, it should be understood that those skilled in the art to which the present invention pertains may variously correct and modify the present invention without departing from the scope of the present invention.

What is claimed is:

1. A heavy metal detecting sensor comprising:
an electrode; and
a plurality of amyloid fibers disposed on the electrode,
wherein an amount of a redox current of the electrode decreases when the plurality of amyloid fibers react with heavy metal ions, and
wherein the electrode includes carbon.

2. The heavy metal detecting sensor of claim 1, wherein the amyloid fiber includes beta-lactoglobulin (β-lactoglobulin).

3. The heavy metal detecting sensor of claim 1, wherein the amyloid fiber includes cysteine, and
wherein a redox reaction of the cysteine is inhibited when the amyloid fibers react with the heavy metal ions.

4. The heavy metal detecting sensor of claim 1, wherein the heavy metal ions are provided in a form of a solution, and the solution including the heavy metal ions has pH in a range of 5.4 to 7.

5. The heavy metal detecting sensor of claim 4, wherein a surface of the amyloid fiber has a negative charge when the amyloid fibers react with the solution including the heavy metal ions.

6. The heavy metal detecting sensor of claim 1, wherein the heavy metal ion includes at least one of palladium ions ($Pd^{2+}$), mercury ions ($Hg^{2+}$), copper ions ($Cu^{2+}$), and cadmium ions ($Cd^{2+}$).

7. A heavy metal detecting method comprising:
preparing a heavy metal detecting sensor including a plurality of amyloid fibers deposited on an electrode;
allowing the heavy metal detecting sensor to react with heavy metal ions; and
sensing a change in an amount of a redox current of the electrode,
wherein the amount of the redox current of the electrode decreases when the amyloid fibers of the heavy metal detecting sensor react with the heavy metal ions.

8. The heavy metal detecting method of claim 7, wherein the amyloid fiber includes cysteine, and
wherein a redox reaction of cysteine is inhibited when the heavy metal detecting sensor reacts with the heavy metal ions.

9. A method of manufacturing a heavy metal detecting sensor, the method comprising:
preparing an amyloid solution including amyloid fibers;
preparing an electrode; and
coating the electrode with the amyloid solution, wherein the coating the electrode is performed for a time of more than 1 minute and not more than 3 minutes.

10. The method of claim 9, wherein the preparing the amyloid solution comprises:
dispersing an amyloid single molecule in an acidic solution to prepare a mixed solution;
filtering the mixed solution; and
heat-treating the mixed solution that is filtered.

* * * * *